US012605270B2

(12) United States Patent
Miller et al.

(10) Patent No.: US 12,605,270 B2
(45) Date of Patent: Apr. 21, 2026

(54) LIQUID AND WASTE COLLECTION SYSTEM

(71) Applicant: Babyation Inc., St. Louis, MO (US)

(72) Inventors: Jared Miller, Chesterfield, MO (US); Samantha Rudolph, Chesterfield, MO (US)

(73) Assignee: Babyation Inc., St. Louis, MO (US)

( * ) Notice: Subject to any disclaimer, the term of this patent is extended or adjusted under 35 U.S.C. 154(b) by 143 days.

(21) Appl. No.: 17/676,028

(22) Filed: Feb. 18, 2022

(65) Prior Publication Data

US 2022/0265463 A1     Aug. 25, 2022

Related U.S. Application Data

(60) Provisional application No. 63/151,660, filed on Feb. 20, 2021.

(51) Int. Cl.
| | |
|---|---|
| *A61F 5/455* | (2006.01) |
| *A61F 5/453* | (2006.01) |
| *A61F 13/15* | (2006.01) |

(52) U.S. Cl.
CPC .............. *A61F 5/455* (2013.01); *A61F 5/453* (2013.01); *A61F 13/15* (2013.01)

(58) Field of Classification Search
CPC ........ A61F 5/455; A61F 5/453; A61F 5/4408; A61F 13/15
See application file for complete search history.

(56) References Cited

U.S. PATENT DOCUMENTS

| | | | | |
|---|---|---|---|---|
| 3,738,363 | A | * | 6/1973 | Lunas ................... A61M 1/062 |
| | | | | 604/319 |
| 4,084,589 | A | | 4/1978 | Kulvi |
| 4,761,160 | A | * | 8/1988 | Vermillion .............. A61M 1/06 |
| | | | | 604/76 |
| 4,840,625 | A | * | 6/1989 | Bell ........................ A61F 5/453 |
| | | | | 604/352 |
| 5,071,403 | A | * | 12/1991 | Larsson .................. A61M 1/06 |
| | | | | 604/320 |
| 6,383,163 | B1 | * | 5/2002 | Kelly ...................... A61M 1/06 |
| | | | | 604/74 |
| 6,706,027 | B2 | | 3/2004 | Harvie |
| 6,740,066 | B2 | | 5/2004 | Wolff |
| 6,918,899 | B2 | | 7/2005 | Harvie |

(Continued)

FOREIGN PATENT DOCUMENTS

| | | | | |
|---|---|---|---|---|
| CN | 104146810 | 11/2014 | | |
| WO | WO2009054944 | 4/2009 | | |
| WO | WO-2014011111 A1 | * 1/2014 | ........... | A61F 5/4405 |

*Primary Examiner* — Ariana Zimbouski
*Assistant Examiner* — Matthew Wrubleski
(74) *Attorney, Agent, or Firm* — Linda Lewis

(57) ABSTRACT

A liquid and waste collection system for collecting liquid has a pressure tubing, a liquid tubing, a pressure source, a liquid container, and a liquid collector. The pressure tubing has a first and second end and the liquid tubing has a first and second end. The first end of the pressure tubing and the first end of the liquid tubing are fluidly connected to the pressure source, and the second end of the pressure tubing and the second end of the liquid tubing are fluidly connected to the liquid collector. The liquid container is fluidly connected on the liquid tubing downstream of the liquid collector, and the liquid does not pass through the pump.

10 Claims, 2 Drawing Sheets

(56)                    References Cited

U.S. PATENT DOCUMENTS

| | | | | |
|---|---|---|---|---|
| 7,018,366 | B2 | 3/2006 | Easter | |
| 7,131,964 | B2 | 11/2006 | Harvie | |
| 7,135,012 | B2 | 11/2006 | Harvie | |
| 7,141,043 | B2 | 11/2006 | Harvie | |
| 7,875,011 | B2 | 1/2011 | Harvie | |
| 10,363,347 | B2 | 7/2019 | Miller | |
| 2001/0044593 | A1* | 11/2001 | Lundy | A41C 3/04 |
| | | | | 604/74 |
| 2002/0026161 | A1* | 2/2002 | Grundke | A61F 5/455 |
| | | | | 604/327 |
| 2004/0230181 | A1 | 11/2004 | Cawood | |
| 2006/0015080 | A1* | 1/2006 | Mahnensmith | A61F 13/15 |
| | | | | 604/327 |
| 2008/0045888 | A1* | 2/2008 | Edwards | A61M 1/068 |
| | | | | 604/74 |
| 2009/0240185 | A1* | 9/2009 | Jaeb | A61M 1/78 |
| | | | | 128/118.1 |
| 2014/0157499 | A1* | 6/2014 | Suzuki | A61G 9/006 |
| | | | | 4/144.3 |
| 2016/0067393 | A1* | 3/2016 | Barnes | A61M 1/06 |
| | | | | 604/74 |
| 2016/0325031 | A1* | 11/2016 | Miller | A61M 1/062 |
| 2019/0314189 | A1* | 10/2019 | Acosta | A61F 5/455 |
| 2019/0365971 | A1* | 12/2019 | Miller | A61M 1/064 |
| 2020/0323739 | A1* | 10/2020 | Mccurren | A61J 9/085 |
| 2022/0040395 | A1* | 2/2022 | Sharma | A61M 1/74 |
| 2022/0378989 | A1* | 12/2022 | Quackenbush | A61M 1/066 |

* cited by examiner

100

LIQUID AND WASTE COLLECTION SYSTEM

CROSS-REFERENCE TO RELATED APPLICATIONS

This application claims the benefit of provisional patent application 63/151,660 filed on Feb. 20, 2021, which is hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

The present invention relates to a fluid collecting system suitable for attachment to living tissue.

More specifically, the present invention relates to a bladder relief system, having a pumping configuration to remove and store urine, where the storage of urine and positioning of the pump are remote from the area of elimination. Further, the system provides a leak-proof system that removes and stores urine without the urine passing through the pump or pump housing.

Related Art

Prior art bladder relief systems are disclosed in U.S. Pat. Nos. 6,706,027, 6,918,899, 7,018,366, 7,131,964, 7,135,012 and 7,141,043. These devices all use a pad or cup secured to the user's body to catch and funnel urine, a tube running from the collector to the pump, and a container to store the store the urine attached to a pump, sometimes by a second tube. All of these use the pump to move the urine, and for all of these references, the urine is pumped through the pump resulting in a need to clean and sanitize the pump. The present bladder relief system provides a urine collecting system where the urine does not pass through the pump.

SUMMARY OF THE INVENTION

The present invention relates to a liquid collection and bladder relief system comprising a pressure source or pump, a power source, a collector interface for male or female anatomy, a urine container, and microprocessor attached to the pump and urine container for receiving and processing data regarding pump settings and urine volume.

The present bladder relief system for collecting urine comprises a pressure tubing, a urine tubing, a pressure source or pump, a urine container, and a urine collector. The present invention further relates to an improved female interface made of a soft plastic or silicone polymer and configured to form a leak proof seal against the vulva, wherein the pressure tubing has a first and second end and the urine tubing has a first and second end. The first end of the pressure tubing and the first end of the urine tubing are fluidly connected to the pump, and the second end of the pressure tubing and the second end of the urine tubing are fluidly connected to the urine collector. The urine container is fluidly connected on the urine tubing between the urine collector and the pump, and the urine does not pass through the pump.

The present invention further comprises a method of using a bladder relief system for collecting urine or other bodily liquids, wherein the bladder relief system comprises a pressure tubing, a liquid tubing, a pressure source, a liquid container, and a liquid collector. The pressure tubing has a first and second end and the liquid tubing has a first and second end. The first end of the pressure tubing and the first end of the liquid tubing are fluidly connected to the pressure source. The second end of the pressure tubing and the second end of the liquid tubing are fluidly connected to the liquid collector. A liquid container is fluidly connected on the liquid tubing between the liquid collector and the pressure source, and the liquid does not pass through the pressure source. The method comprises applying the liquid collector to a user, collecting liquid in the liquid collector, and using the pressure source to push air to the pressure tubing to create a positive pressure. The positive pressure moves the liquid from the liquid collector to the liquid tubing, the liquid moves from the liquid tubing to the liquid container, and the liquid is collected in the liquid container.

The present invention further comprises a bodily fluid or waste collecting system suitable for attachment to surfaces, such as living tissue, such as skin or membranes. The system for collecting liquid comprising an air tubing, a liquid tubing, a pressure source, a separating chamber, a liquid container and a liquid collector. The separating chamber has an air port, a liquid output and a liquid input. The air tubing has a first and second end, and the liquid tubing has a first and second end. The first end of the air tubing is fluidly connected to the pressure source, and the second end of the air tubing is fluidly connected to the air port of the separating chamber. The first end of the liquid tubing is connected to the liquid collector, and the second end of the liquid tubing is connect to the liquid input of the separating chamber. The liquid collector seals against the surface. The liquid container is fluidly connected to the liquid output of the separating chamber. The pressure source can be used to create a positive pressure or a negative pressure, or both a positive pressure and a negative pressure to move liquid in the liquid tubing. The liquid does not pass through the pressure source.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 1:
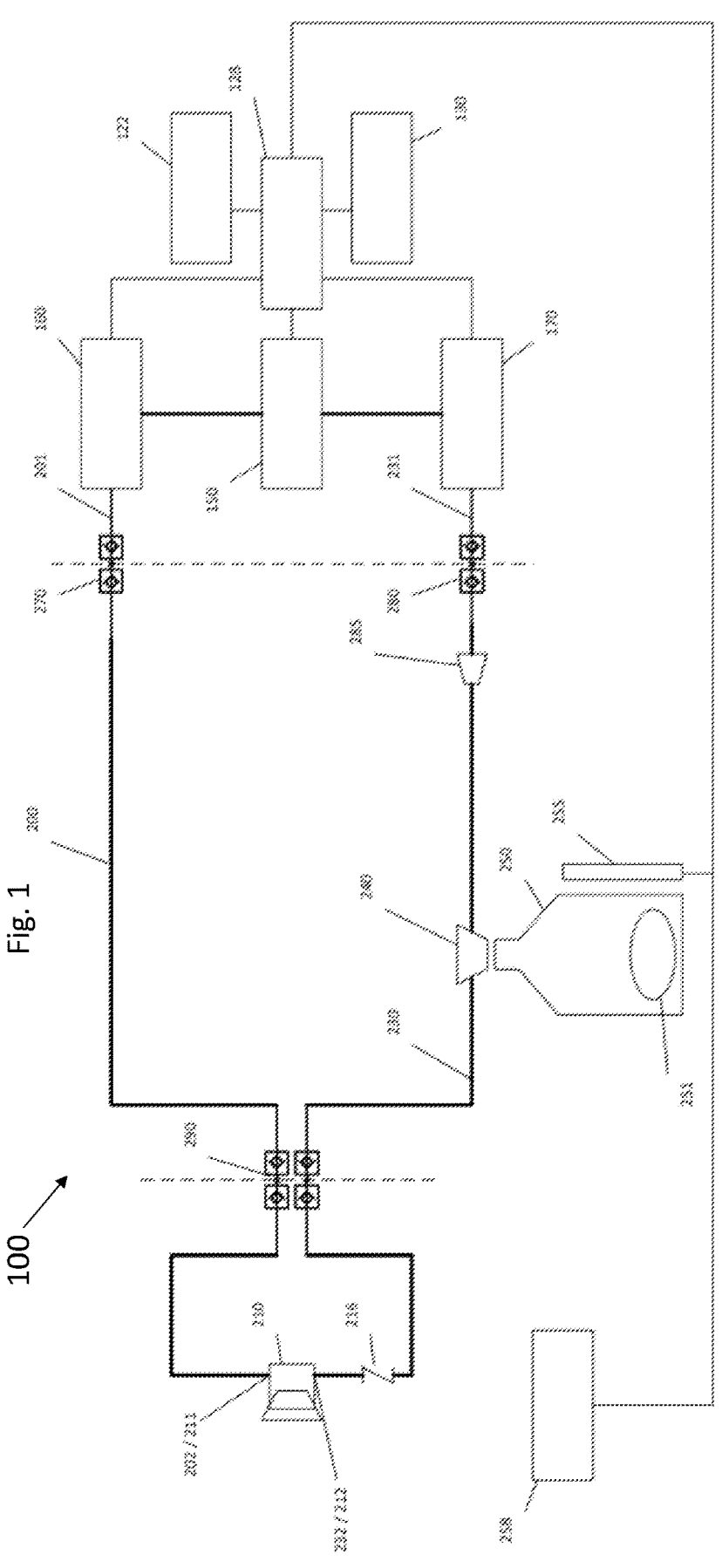
FIG. 1 is a schematic of a first embodiment of the present liquid collecting system.

In FIG. 1, a first embodiment of the bladder relief system 100 wherein the liquid is urine. It has a pneumatic pump or pressure source such as a pressurized air tank 150 attached to a power source 130 and a controller 128. Fluidly attached to the pump 150 is either a positive pressure system and/or a negative pressure system. The positive pressure system is comprised of an electronically controlled solenoid valve 160 fluidly attached to the pump 150 output and the pressure tubing 200. The negative pressure system is comprised of an electronically controlled solenoid valve 170 fluidly attached to the pump 150 suction port and the liquid tubing 230. In additional embodiments, the pump, controller, and power source could be replaced with an air cartridge pressure source and pneumatic regulator. In yet additional embodiments, the vacuum system could be comprised of a venturi vacuum generator to generate negative pressure from an alternative pressure source. Fluidly attached to the positive pressure system is the first end 201 of the pressure tubing 200. Fluidly attached to the negative pressure system is the first end 231 of the liquid tubing 230. The second end 202 of the pressure tubing is fluidly attached to the first port 211 of the on-body liquid collector 210. The second end 232 of the liquid tubing 230 is fluidly attached to the second port 212 of the on-body liquid collector 210. Optionally, the tubing ends 202 and 232 could be releasably connected to ports 211 and 212 via a connector to allow ease of removal and cleaning of the parts. Optionally, connector system 290 provides an additional releasable mechanism for pressure tubing 200 and liquid tubing 230 to pass through a clothing garment, such as an aviator flight suit. Optionally, a check valve 216 blocks the backflow of liquid to the liquid collector 210. The check valve can be located in the liquid collector, or between the liquid collector and the liquid tubing, or as part of the liquid tubing. Between the first and second ends 231 and 232 is the liquid container 250 with an inline attachment device 240. Optionally, between the liquid container 250 and the negative pressure valve 170 is a self-sealing liquid and bacterial filter 285. The liquid does not pass through the pump 150. Optionally, the liquid container 250 may contain a gelling agent 251 to convert the liquid liquid to a gel form for ease of storage. The gelling agent may optionally be stored in a water-soluble pouch to be released upon contact with the liquid.

It is understood that the flow of liquid to the storage container is facilitated by differential pressure in the system and that there are different embodiments that will result in the same flow, such as using a positive pressure system to apply pressure to the pressure tubing to push liquid down the liquid tubing; or using a negative pressure system to apply suction to the liquid tubing to pull the liquid down the liquid tubing; or using both positive and negative pressure to both push and pull the liquid.

Optionally, the pressure tubing 200 and the liquid tubing 230 can have connectors 270 and 280, respectively. This allows the liquid collector 210 and the liquid container 250 to be disconnected from the rest of the device for cleaning. In a preferred embodiment, the remainder of the device 100 that is disconnected is enclosed in a pump housing (not shown) for convenience. The user can interact with the system via user interface 122 which may be comprised of controls on the exterior of the pump housing. In an additional embodiment, the user interface could be comprised of an application on a remote device communicating over a wireless implementation, such as using Bluetooth Low Energy.

Optionally, sensors such as a liquid level sensor 255 to measure the amount of liquid in the container or a hydration sensor 258 worn by the user could be interfaced to the controller to record various parameters. Additional sensors to measure various properties of the collected liquid could also be interfaced. These sensors could be directly connected to the controller or interfaced remotely.

Method of Operation

The pump 150 is activated and the optional positive pressure system applies positive air pressure to the pressure tubing 200 which applies air pressure to the liquid collector 210. When liquid is caught, the positive air pressure moves the liquid from the liquid collector into the liquid tubing 230 toward the liquid container 250. When urination is completed, this creates a flow of drying air across the liquid collector and user.

The optional negative pressure system provides negative air pressure to the liquid tubing via negative pressure valve 170, allowing negative air pressure to be applied to the liquid container 250 and the liquid tubing 230. Liquid is drawn from the liquid collector through the liquid tubing 230 to the liquid container 250. Liquid does not pass into the pump.

The liquid collector 210 can be a male interface or a female interface. The female interface interfaces sealingly with the surface of the vulva to transfer suction to the vulva area and to direct the flow of liquid away from the vulva to the liquid tubing and liquid collection container. The female interface could be of a larger size targeting the full vulva, or a smaller size targeting the urethra directly. Likewise, the male interface seals against the base of the penis to transfer suction to the penis area. The interface is made of a soft silicone rubber or plastic polymer and is designed to fit comfortably and securely.

The present bladder relief system can be controlled wirelessly by an app on a user's smart phone or other digital device or by a front-panel display and controls or started automatically upon the detection of liquid flow. Further, the pump system may capture the detail of the volume of liquid produced in a given time period and may record other parameters acquired by various sensors. This data is uploaded from the app to an Internet cloud service for storage, analysis and retrieval to display. The app also may track duration, frequency and volume of liquid produced.

The bladder relief system 100 can have custom settings entered by the user. Optional presets are provided that may be helpful to the user. The present bladder relief system has the collection container and the pump fluidly and remotely connected to the liquid collector by lengths of tubing. In a preferred embodiment, clothing and undergarments cover and engage with the liquid collector and tubing. This provides a discreet system that can be worn under a user's clothing.

Figure 2:
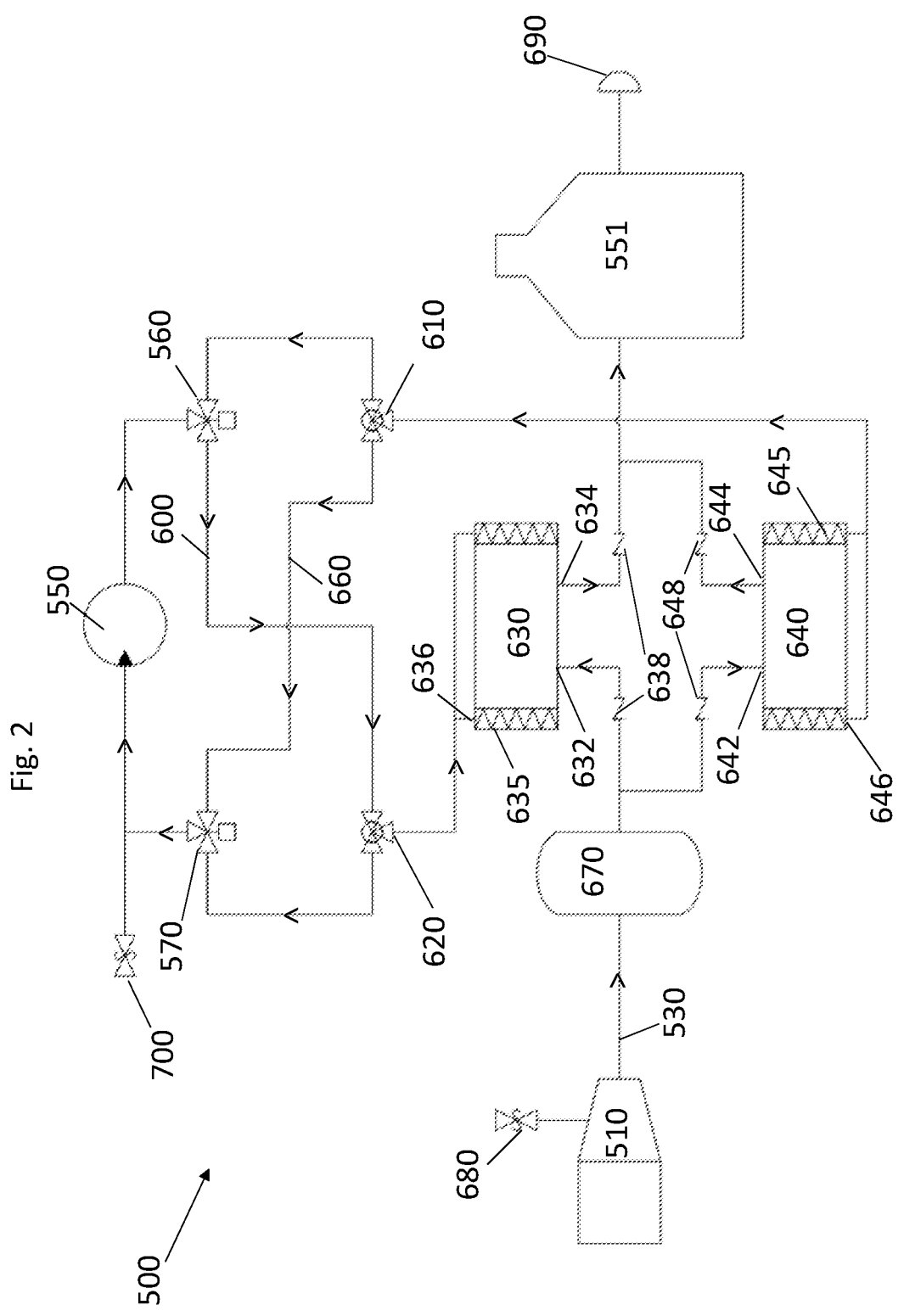
FIG. 2 is a schematic of a second embodiment of the present liquid collecting system.

As shown in FIG. 2, a second embodiment of the liquid collecting system 500 has a liquid handling portion of the system comprising a liquid collector, at least one separating chamber, and a liquid container. The collecting system also has an air handling portion of the system comprising the pump or pressure source, the pressure solenoid valves, and the air manifolds. The liquid collecting system uses pressure from the air handling portion of the system to remove liquid, but the liquid never passes through the air handling portion of the system or pump. The at least one separating chamber has at least one air port, a liquid output and a liquid input. In a preferred embodiment, there are two separating chambers, each of which has two air ports. The separating chambers isolate the liquid from the air handling system, using hydrophobic filters, which prevents liquid from flowing to the air handling portion of the system. The separating chambers have a hard-sided construction that withstand fluctuating pressures without collapsing. The separating chambers allow the use of a soft-sided liquid container that will not withstand negative pressure without collapsing, because negative pressure is not applied to the liquid container. The at least one separating chamber is filled and emptied repeatedly, thereby moving the aqueous fluids from the liquid collector to the liquid container. In a more preferred embodiment, there are two or more separating chambers where, as one chamber is filled, the second chamber is emptied. This two separating chamber system provides faster pumping of the aqueous fluids than the system with one separating chamber. The liquid moves into the separating chambers from the liquid collection interface and from the separating chambers into the liquid container of the liquid collecting system.

In FIG. 2, the liquid collecting system has a pneumatic pump or pressure source such as a pressurized air tank 550 attached to a power source (not shown) and a controller (not shown). Fluidly attached to the pump 550 is either a positive pressure system and/or a negative pressure system. Both a positive pressure system and a negative system are shown, working together. This is a hybrid system.

The positive pressure system is comprised of an electronically controlled positive pressure solenoid valve 560 fluidly attached to the pump 550 output and the positive pressure tubing 600. The positive pressure tubing connects the positive pressure valve to the manifold 620. The manifold is fluidly connected to the separating chamber 630 at the air port 636 which is attached to the hydrophobic filter 635. The separating chamber has at least one hydrophobic filter 635 which allows passage of gases but not aqueous liquids (such as urine). A preferred hydrophobic filter is a one micron PTFE filter. The liquid leaves the positive pressure separating chamber at the liquid output 634. The liquid output is fluidly connected to the liquid container 551. Optionally, between the liquid output and the liquid container is a check valve 638 to prevent back flow of liquid, such as when the separating chamber is at a lower pressure than the liquid container.

The negative pressure system is comprised of an electronically controlled negative pressure solenoid valve 570 fluidly attached to the pump 550 suction port and the negative pressure tubing 660. The negative pressure tubing connects the negative pressure valve to the manifold 620. The manifold is fluidly connected to the separating chamber 630 at the air port 636 which is connected to the hydrophobic filter 635. Optionally, a vacuum relief valve 700 is fluidly connected to the pump suction port and configured to provide makeup air in the event that the system is internally blocked by liquid.

The system operates by using negative pressure solenoid valve 570 to connect the pressure source 550 suction port to the separating chamber 630 for a period of time. In some embodiments, this is configured to be about 2 seconds. During this time, air is removed from the chamber resulting in the chamber becoming negatively pressurized. Air and any entrained liquid is drawn from the collection interface 510 toward the collection chamber 630 via liquid tubing 530. During this time, the positive pressure solenoid valve 560 is configured to exhaust the pump to atmosphere. After this period of time, the system is configured to reverse the airflow to the separating chamber 630 by using negative pressure valve 570 to direct the pump suction to atmosphere and by using positive pressure valve 560 to direct the pump exhaust to the separating chamber. During this time period of time with reverse flow, the chamber becomes positively pressurized, causing liquid to exit liquid output port 634 toward liquid collection 551.

Optionally, the system can be configured with one or more additional separating chambers 640 with corresponding filter 645, air port 646, liquid ports 642 and 644, and check valves 648. In such an embodiment, the negative pressure solenoid valve 570 and positive pressure solenoid valve 560 would connect to the additional separating chamber 640 via additional manifold 610 instead of exhausting to atmosphere. In this configuration, the efficiency of the system is increased in that the additional separating chamber is being positively pressurized by the air that is being removed from the first separating chamber 630, instead of exhausting the air to atmosphere. The reverse flow is also made similarly more efficient. A further benefit is that the airflow from liquid collection interface 510 is more continuous instead of pulsed.

The number of separating chambers is from one to about ten. In a preferred embodiment, the number of separating chambers is about 2 to 4.

The liquid collection interface 510 is fluidly connected to the separating chamber at the liquid input 632. Optionally, between the liquid collection interface and the separating chambers is a liquid surge container 670, to modulate volume during high flow conditions. Further optionally, a check valve 638 can be positioned between the liquid collection interface and the separating chamber to prevent back flow of liquid to the liquid collection, such as when the separating chamber 630 is at a higher pressure than the liquid collection interface 510.

Optionally, the liquid collection interface has a vacuum relief valve 680 to prevent excess suction and discomfort. The relief valve is configured to establish the maximum suction level that is applied to the user. Optionally, the liquid storage container has a relief filter or valve 690 to vent gasses carried by the liquid and prevent over pressurization of the liquid container.

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A liquid collecting system comprising an air tubing, a liquid tubing, a pressure source, at least one separating chamber, a liquid container and a liquid collector;
    wherein the liquid is liquid from a surface;
    wherein the at least one separating chamber comprises an air port, a liquid output and a liquid input;
    wherein the at least one separating chamber comprises a filter that separates the air port from the liquid input and the liquid output;
    wherein the construction of the at least one separating chamber is hard-sided and withstands fluctuating pressures without collapsing;
    wherein the air tubing has a first and second end and the liquid tubing has a first and second end;

wherein the first end of the air tubing is fluidly connected to the pressure source;

wherein the second end of the air tubing is fluidly connected to the air port of the at least one separating chamber;

wherein the first end of the liquid tubing is connected to the liquid collector;

wherein the second end of the liquid tubing is connected to the liquid input of the at least one separating chamber;

wherein the at least one separating chamber separates the air from the liquid;

wherein the liquid collector seals against the surface;

wherein the liquid container is fluidly connected to the liquid output of the at least one separating chamber;

wherein negative pressure is not applied to the liquid container;

wherein the pressure source can be used to create a positive pressure or a negative pressure, or both a positive pressure and a negative pressure to move fluid in the liquid tubing from the liquid collector to the liquid container;

wherein the liquid container and the pressure source are fluidly and remotely connected to the liquid collector by either the liquid tubing and/or the pressure tubing;

wherein the liquid does not pass through the pressure source;

and wherein the at least one separating chamber comprises from two to four separating chambers physically separated from one another via tubing.

2. The liquid collecting system of claim 1, wherein the at least one separating chamber filter comprises a hydrophobic filter that allows air to filter out but prevents liquid from entering the air port.

3. The liquid collecting system of claim 2, wherein the system is a hybrid system having both the positive pressure and the negative pressure.

4. The liquid collecting system of claim 1, wherein the liquid container is soft-sided and collapses with negative pressure.

5. A liquid collecting system comprising an air tubing, a liquid tubing, a pressure source, at least one separating chamber, a liquid container and a liquid collector;

wherein the liquid is liquid from a human or animal body;

wherein the at least one separating chamber has an air port, a liquid output and a liquid input;

wherein the air port of the at least one separating chamber comprises at least one hydrophobic filter, wherein the hydrophobic filter allows air to filter out;

wherein the construction of the at least one separating chamber is hard-sided and withstands fluctuating pressures without collapsing;

wherein the air tubing has a first and second end and the liquid tubing has a first and second end;

wherein the first end of the air tubing is fluidly connected to the pressure source;

wherein the second end of the air tubing is fluidly connected to the air port of the at least one separating chamber;

wherein the first end of the liquid tubing is connected to the liquid collector;

wherein the second end of the liquid tubing is connected to the liquid input of the at least one separating chamber;

wherein the at least one separating chamber separates the air from the liquid;

wherein the liquid collector seals against the body;

wherein the liquid container is fluidly connected to the liquid output of the at least one separating chamber;

wherein negative pressure is not applied to the liquid container;

wherein the pressure source can be used to create a positive pressure or a negative pressure, or both a positive pressure and a negative pressure to move fluid in the liquid tubing from the liquid collector to the liquid container;

wherein the liquid container and the pressure source are fluidly and remotely connected to the liquid collector by either the liquid tubing and/or the pressure tubing;

wherein the liquid does not pass through the pressure source;

and wherein the at least one separating chamber comprises from two to four separating chambers physically separated from one another via tubing.

6. The liquid collecting system of claim 5, wherein the system is a hybrid system having both positive pressure and negative pressure.

7. The liquid collecting system of claim 6, wherein the pressure source is a pump.

8. The liquid collecting system of claim 5, wherein the liquid is urine; and wherein the liquid collector is selected from the group consisting of a male interface or a female interface.

9. The liquid collecting system of claim 8, wherein the female interface interfaces sealingly with a surface of a vulva; and wherein the male interface interfaces sealingly with a base of a penis.

10. The liquid collecting system of claim 5, wherein the liquid container is soft-sided and collapses with negative pressure.

* * * * *